United States Patent [19]

Sarantakis

[11] 4,253,998
[45] Mar. 3, 1981

[54] PEPTIDES RELATED TO SOMATOSTATIN

[75] Inventor: Dimitrios Sarantakis, West Chester, Pa.

[73] Assignee: American Home Products Corporation, New York, N.Y.

[21] Appl. No.: 19,216

[22] Filed: Mar. 9, 1979

Related U.S. Application Data

[63] Continuation-in-part of Ser. No. 899,438, Apr. 24, 1978, abandoned.

[51] Int. Cl.$^2$ .................... C08L 37/00; C07C 103/52; A61K 37/00
[52] U.S. Cl. ................... 260/8; 260/112.5 S; 424/177
[58] Field of Search ............... 260/112.5 S, 8; 424/177

[56] References Cited

U.S. PATENT DOCUMENTS

| | | | |
|---|---|---|---|
| 4,011,207 | 3/1977 | Sarantakis | 260/112.5 S |
| 4,061,608 | 12/1977 | Sarantakis | 260/112.5 S |
| 4,077,952 | 3/1978 | Sarantakis | 260/112.5 S |
| 4,100,153 | 7/1978 | Garsky | 260/112.5 S |
| 4,104,267 | 8/1978 | Sarantakis | 260/112.5 S |
| 4,122,077 | 10/1978 | Sarantakis | 260/112.5 S |
| 4,133,782 | 1/1979 | Vale, Jr. et al. | 260/112.5 S |

FOREIGN PATENT DOCUMENTS 839405  10/1976  Belgium ............... 260/112.5 S

OTHER PUBLICATIONS

Rivier, et al., J. Med. Chem. 18, 123 (1975).
Rivier, et al., Biochem. Biophys. Res. Commun. 65, 746 (1975).
Coy, et al., "58th Annual Meeting of the Endocrine Society", San Francisco, Calif., Abst. 305, p. 209.
Brown, et al., Science, 196 1467 (1977); and Meyer, Biochem. Biophys. Res. Commun. 74, 630 (1977).

Primary Examiner—Delbert R. Phillips
Attorney, Agent, or Firm—Arthur G. Seifert

[57] ABSTRACT

Peptides of the formula:

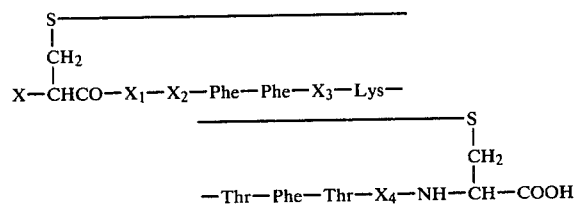

wherein:
X is H, $-NH_2$, $-NH-Gly-Ala$, $-NH-D-Ala-Ala$, $-NH-Gly-Gly-Gly$, $-NH-$acetyl, or $-NH-$benzoyl;
$X_1$ is His or Arg;
$X_2$ is His, Glu, Tyr, Trp, or Phe;
$X_3$ is Trp, D-Trp, or 6-F-D-Trp; and
$X_4$ is a D-α-amino acid;

or the reduced, linear form thereof, or a non-toxic, pharmaceutically acceptable acid addition salt thereof; inhibit the release of growth hormone, insulin, and glucagon; and show prolonged inhibition activity. Said peptides are prepared by solid-state methodology.

9 Claims, No Drawings

PEPTIDES RELATED TO SOMATOSTATIN

CROSS-REFERENCE TO RELATED APPLICATION

This application is a continuation-in-part of co-pending application Ser. No. 899,438, filed Apr. 24, 1978, now abandoned.

This invention related to synthetic peptides structurally related to somatostatin and to intermediates employed in the synthesis thereof. In the compounds of the invention, the somatostatin peptide chain is modified at the 4, 5, and 13 position, with the 1, 2, 8, and 14 positions being preferably modified also.

Somatostatin is the cyclic disulfide tetradecapeptide of the formula:

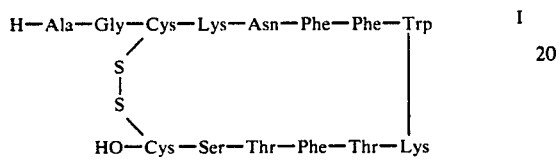

This peptide (I) has been identified as the "somatotropin-release inhibiting factor" (SRIF) which is secreted by the hypothalamus and regulates the secretion of pituitary growth hormone (GH) (somatotropin). [See Brazeau et al., Science, 179, 77 (1973), Burgus et al., Proc. Nat. Acad. Sci. (USA), 70, 684 (1973), and Ling et al., Biochemical and Biophysical Res. Communication, 50, 127 (1973)]. The reduced form of somatostatin (RS) is the linear tetradecapeptide of the formula:

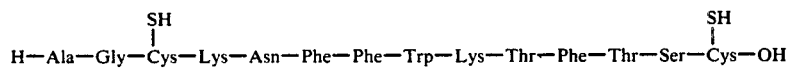

The reduced form (II) has been prepared by total synthesis, [see Rivier et al., C. R. Acad. Sci. Ser. p. Sci. Natur. (Paris), 276, 2737 (1973) and Sarantakis and McKinley, Biochem. and Biophys. Res. Communications, 54, 234 (1973)] and it (II) can be converted to somatostatin (I) by oxidation whereby a bridging bond is formed between the two sulfhydryls of the two cysteinyl amino acid residues in the tetradecapeptide.

Various polypeptides which may be regarded as structural modifications of somatostatin have been prepared synthetically and are reported in the chemical literature. Such polypeptides have certain structural features in common with somatostatin and differ from somatostatin in that specific amino acid residues or functional groups originally present in the somatostatin molecule are either missing or are replaced by other amino acid residues or functional groups. The present invention relates to novel synthetic biologically active polypeptides which may be regarded as a structural modification of somatostatin. The polypeptides of the invention differ from somatostatin in the following respects:

(a) the $Ala^1$-$Gly^1$ segment is either present, missing, or replaced by Gly-Gly-Gly, Ala-D-Ala, acetyl, or benzoyl;

(b) the $Cys^3$ residue is either present or replaced by a $\beta$-mercaptopropionic acid residue;

(c) the $Lys^4$ residue is replaced by Arg or His;

(d) the $Asn^5$ residue is replaced by His, Glu, Tyr, Trp, or Phe; and (e) the $Trp^8$ residue is either present or replaced by D-Trp or 6-F-D-Trp;

(f) the $Ser^{13}$ residue is replaced by a D-$\alpha$-amino acid residue; and (g) the $Cys^{14}$ residue is either present or replaced by D-Cys. Modifications of somatostatin missing the $Ala^1$-$Gly^2$ segment and the N-terminal amino group are reported by Rivier et al., J. Med. Chem., 18, 123 (1975). Replacement of the $Trp^8$ residue by D-Trp is discussed by Rivier et al., Biochem. Biophys. Res. Commun., 65, 746 (1975). Modifications of somatostatin wherein the $Lys^4$-$Asn^5$ segment are replaced with other amino acid residues are disclosed in Belgian Pat. 839,405. A modification of somatostatin wherein D-serine is substituted for $Ser^{13}$ is described by Coy et al., "58th Annual Meeting of the Endocrine Society," San Francisco, California, Abstract 305, page 209. D-$Trp^8$, D-$Cys^{14}$-Somatostatin is described by Brown et al., Science, 196, 1467 (1977) and Meyer, Biochem. Biophys. Res. Commun., 74, 630 (1977).

The invention sought to be patented comprises a peptide of Formula III:

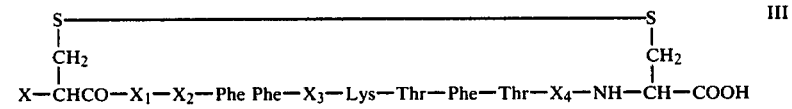

wherein
X is H, —$NH_2$, —NH—Gly-Ala, —NH-D-Ala-Ala, —NH-Gly-Gly-Gly, NH-acetyl, or —NH-benzoyl;

$X_1$ is His or Arg;

$X_2$ is His, Glu, Tyr, Trp, or Phe;

$X_3$ is Trp, D-Trp, or 6-F-D-Trp; and $X_4$ is a D-$\alpha$-amino acid;

or a non-toxic, pharmaceutically acceptable acid addition salt thereof.

In addition, this invention contemplates the linear form of the compounds of Formula III (i.e. the non-cyclic reduced compounds of Formula IV which differ in that they contain two free sulfhydryl groups), or a non-toxic acid addition salt thereof.

The linear peptides of Formula IV are precursors for the cyclic peptide of Formula III.

All optically active amino acids and amino acid residues in the polypeptides depicted and described herein are in the natural or L-configuration, unless otherwise noted. The symbols identifying the amino acids and the amino acid residues in the polypeptides described herein are those adopted by the IUPAC-IVB Committee on Biochemical Nomenclature Recommendation (1971), and are described in the Archives of Biochemistry and Biophysics, 150, 1-8 (1972). The symbol "6-F-D-Trp" means D-tryptophan in which the 6-position is substituted by fluorine. The term "D-α-amino acid" means an optically active α-amino acid in which the α-carbon is in the D-configuration. Preferred examples of such D-amino acids are: D-proline, D-alanine, D-valine, D-leucine, D-isoleucine, D-serine, D-threonine, D-methionine, D-aspartic acid, D-glutamic acid, D-lycine, D-arginine, D-asparagine, D-histidine, D-tryptophan, D-phenylalanine, and D-tyrosine.

It will be apparent to those skilled in the art that the α-carbon of the cysteine residues (corresponding to $Cys^3$ and $Cys^{14}$ of somatostatin) contain an assymetric carbon atom and optical isomers of such amino acid residues are possible. In the peptides depicted by the formulae set forth herein (Formula III, IV, or V), the $Cys^3$ residue must be in the natural (L-) configuration, while the $Cys^{14}$ residue can be in either the natural (L-) or un-natural (D-) configuration.

The compounds of Formula III and IV inhibit the secretions of growth hormone, insulin, and glucagon as demonstrated in standard pharmacological test procedures, and are useful in controlling serum glucose in the treatment of diabetes. These compounds also show a prolonged period of action.

A preferred embodiment of the compounds of Formula III and IV is that wherein X is $NH_2$; $X_1$ is Arg; $X_2$ is His; $X_3$ is D-Trp; and $X_4$ is D-Tyr. The method of preparation of the above embodiment is described in Examples 1 and 2. Another preferred embodiment of the compounds of Formula III and IV is that wherein X is $NH_2$; $X_1$ is Arg; $X_2$ is Glu; $X_3$ is D-Trp; and $X_4$ is D-Tyr, which inhibits the release of growth hormone and insulin without materially inhibiting the release of glucagon. The preparation of this embodiment is described in Examples 3 and b 4. A further preferred embodiment of the compounds of Formula III and IV is that wherein X is $NH_2$; $X_1$ is His; $X_2$ is His; $X_3$ is D-Trp; and $X_4$ is D-Ser, which inhibits the release of growth hormone and glucagon without materially inhibiting the release of insulin. The preparation of this embodiment is described in Examples 5 and 6. Other embodiments can be prepared using similar methods or obvious modifications thereof. A desired embodiment can be prepared using the exemplified technique by substituting a desired protected amino acid for a particular moiety illustrated.

The polypeptides of this invention are prepared by the solid phase method following techniques generally known in the art for building an amino acid sequence from an initial resin-supported C-terminal amino acid. Such techniques are described by J. M. Stewart et al., Solid Phase Peptide Synthesis, Freeman and Co., San Francisco, 1969. As applied to the synthesis of the polypeptides of Formula III and IV, the initial C-terminal amino acid is L- or D-cysteine, and the resin support preferably a chloromethylated polystyrene resin. The chloromethyl groups provide sites for attachment of L- or D-cysteine to the resin support by means of ester formation.

In carrying out the synthesis, the chloromethylated polystyrene resin is esterified with α-amino and sulfhydryl protected D- and L-cysteine (e.g. Boc-Cys(SMBzl)-OH) according to the procedure of Gisin, Helv. Chim. Acta., 56, 1476 (1973). The protected amino acid is linked by ester formation between the carboxyl group of L- or D-cysteine and a chloromethyl group of the resin. The α-amino protecting group is then removed with trifluoroacetic acid in methylene chloride, trifluoroacetic acid alone or hydrogen chloride in dioxane. The deprotection is conducted at a temperature between about 0° C. and room temperature. Other standard cleaving reagents and conditions for removal of specific α-amino protecting groups may be used as described in Schroder E. Lubke, "The Peptides," 1, 72-75 (Academic Press, 1965). After removal of the α-amino protecting group, the subsequent protected amino acids are coupled individually to the resin supported sequence, seriatim. Alternatively, small peptide fragments may be prepared by the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., Analyt. Biochem., 34, 595 (1970). Where incomplete coupling has occurred, the reaction is repeated before the α-amino protecting group is removed for introduction of the next amino acid sequence. Diisopropylcarbodiimide is a preferred coupling reagent, although other agents will be apparent to those skilled in the art.

After the desired amino acid sequence has been synthesized, the polypeptide is removed from the resin support by treatment with hydrogen fluoride and anisole to obtain the fully deprotected linear polypeptide. The cyclic disulfide is produced by oxidation of the linear polypeptide, such as by treatment with $K_4Fe(CN)_6$ or by contact with air.

Non-toxic acid addition salts of the linear and cyclic polypeptides are produced by methods well-known in the art from organic or inorganic acids which are nontoxic and acceptable for pharmaceutical purposes, such as hydrochloric, hydrobromic, sulfuric, phosphoric, polyphosphoric, maleic, acetic, citric, benzoic, succinic, malonic, or ascrobic acid and the like.

The protecting groups employed throughout the solid phase synthesis are well-known to the art. In selecting a particular side-chain protecting group to be used in the synthesis of the peptides of this invention, the following rules should be followed: (a) the side-chain protecting group must be stable to the reagent and under the reaction conditions selected for removing the α-amino protecting group at each step of the synthesis; (b) the protecting group must retain its protecting properties (i.e. not be split off under coupling conditions); and (c) the side-chain protecting group must be removable upon the completion of the synthesis containing the desired amino acid sequence under reaction conditions that will not alter the peptide chain.

Preferred protecting groups for the amino acids employed in the solid state synthesis are as follows: (a) for an α-amino group: t-butyloxycarbonyl (BOC); (b) for a side-chain hydroxyl group: benzyl (Bzl); (c) for a side-chain aromatic hydroxyl group: 2,6-dichlorobenzyl (Cl$_2$Bzl); (d) for a side-chain carboxyl group: benzyl (Bzl); (e) for a side-chain ω-amino group: 2-chlorobenzyloxycarbonyl (ClZ); (f) for the side-chain guanidine nitrogens: tosyl (Tos); (g) for the secondary imidazol nitrogen: tosyl (Tos); and (h) for a side-chain mercapto group: p-methoxybenzyl (MBzl).

In addition to the pharmacologically active polypeptides of Formula III and IV, the present invention also includes the novel peptide-resin intermediates of Formula V:

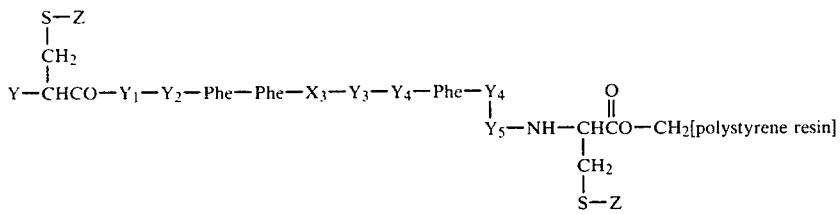

wherein:
(a) $X_3$ is Trp, D-Trp, or 6-F-D-Trp;
(b) Y is H, —NH(R), —NH-Gly-Ala(R), —NH-Gly-Gly-Gly(R), —NH-D-Ala-Ala(R), —NH-acetyl, or —NH-benzoyl;
(c) $Y_1$ is His($R_1$) or Arg($R_1$);
(d) $Y_2$ is His($R_1$); Glu($R_2$), Tyr($R_3$), Trp, or Phe;
(e) $Y_3$ is Lys($R_4$);
(f) $Y_4$ is Thr($R_5$);
(g) $Y_5$ is D-Pro, D-Ala, D-Val, D-Leu, D-isoLeu, D-Ser($R_5$), D-Thr($R_5$), D-Asp($R_2$), D-Glu($R_2$), D-Lys($R_4$), D-Arg($R_1$), D-Asn, D-His($R_1$), D-Trp, D-Phe, or D-Tyr($R_3$); and
(h) Z is the p-methoxybenzyl protecting group; wherein R is an α-amino protecting group and $R_1$, $R_2$, $R_3$, $R_4$, and $R_5$ are each, independently, a side-chain protecting group.

Preferred protecting groups are those in which:
R is t-butyloxycarbonyl;
$R_1$ is tosyl;
$R_2$ is benzyl(ester);
$R_3$ is 2,6-dichlorobenzyl;
$R_4$ is 2-chlorobenzoyloxycarbonyl; and
$R_5$ is benzyl(ether).

In the compounds of Formula V, the polystyrene resin may be any suitable resin support conventionally employed in the art for the solid-phase synthesis of polypeptides, preferably polystyrene which has been crossed linked with from 0.5 to about 3% divinyl benzene, which has been chloromethylated or hydroxymethylated to provide sites for ester formation between the initially introduced α-amino protected L- or D-cysteine. A chloromethylated polysturene resin is commercially available for Bio Rad Laboratories, Richmond, California, and the preparation of such a resin is described by Stewart et al., "Solid Phase Peptide Synthesis," Freeman and Co., San Francisco, 1969, Chapter 1, pages 1-6. In Formula V,

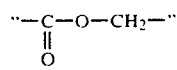

represents the ester linkage between the c-terminal carboxy group of the polypeptide and one of the many methylene groups originally introduced into the phenyl moieties of the polystyrene chain by chloromethylations.

The compounds described herein may be administered to warm-blooded mammals, either intravenously, subcutaneously, intramuscularly, or orally to control serum glucose in the treatment of diabetes or hyperinsulinemia. The required dosage will vary with the particular condition being treated, the severity of the condition and the duration of treatment.

The active ingredient may be administered alone or in combination with pharmaceutically acceptable carriers or excipients. Suitable pharmaceutical compositions will be apparent to those skilled in the art.

The methods of making and using the compounds of the invention are illustrated in the following examples:

EXAMPLE 1 tert-Butyloxycarbonyl-S-p-Methoxybenzyl-L-Cysteinyl-N$^g$-Tosyl-L-Arginyl-N$^{im}$-Tosyl-L-Histidyl-L-Phenylalanyl-L-Phenylalanyl-D-Tryptophyl-N$^ε$-2-Chlorobenzyloxycarbonyl-L-Lysyl-O-Benzyl-L-Threonyl-L-Phenylalanyl-O-Benzyl-L-Threonyl-O-2,6-Dichlorobenzyl-D-Tyrosyl-S-p-Methoxybenzyl-L-Cysteinyl-Hydroxymethyl-Polystyrene Ester Chloromethylated polystyrene resin [Lab Systems, Inc.] (0.75 meq. per g.) is esterified with Boc-Cys(SMBzl)-OH cesium salt, according to the procedure of Gisin, Helv. Chim. Acta., 56, 1976 (1973). The amino acid resin was then treated according to Schedule A (set forth below), Boc-D-Tyr(Cl$_2$Bzl)-OH being employed as the protected amino acid in Step 9 thereof. Schedule A was then repeated as necessary in order to incorporate consecutively the following amino acids into the peptido resin:

Boc-Thr(Bzl)—OH
Boc-Phe-OH
Boc-Thr(Bzl)—OH
Boc-Lys(ClZ)—OH
Boc-D-Trp—OH
Boc-Phe—OH
Boc-Phe—OH
Boc-His(Tos)—OH
Boc-Arg(Tos)—OH
Boc-Cys(SMBzl)—OH

Schedule A: [protocol for the deprotection of the α-amino group and coupling of the protected amino acids on the Boc-Cys(SMBzl)—O—CH$_2$-(protected resin)]
1. Wash with methylene chloride (CH$_2$Cl$_2$), three times.
2. Treat with trifluoroacetic acid-methylene chloride 9:1, v/v) containing 5% 1,2-ethane dithiol for 5 minutes.
3. Repeat Step 2 for 25 minutes.
4. Wash with CH$_2$Cl$_2$, three times.
5. Wash with dimethylformamide (DMF).
6. Treat with 12% triethylamine in DMF for 3 minutes.
7. Wash with DMF.

8. Wash with CH₂Cl₂, three times.
9. Treat with 4 equivalents of the appropriate protected amino acid in CH₂Cl₂-DMF and stir for 5 minutes.
10. Add in two portions over a 30 minute period 5 equivalents of diisopropylcarbodiimide dissolved in CH₂Cl₂. Allow reaction to procede for 6 hours.
11. Wash with DMF, three times.
12. Wash with CH₂Cl₂, three times.
13. Test by ninhydrin reaction according to the procedure of Kaiser et al., Annal. Biochem., 34, 595 (1970). In case of incomplete reaction, repeat Steps 9 to 13, as above.

EXAMPLE 2

L-Cysteinyl-L-Arginyl-L-Histidyl-L-Phenylalanyl-L-Phenylalanyl-D-Tryptophyl-L-Lysyl-L-Threonyl-L-Phenylalanyl-L-Threonyl-D-Tyrosyl-L-Cysteine Cyclic (1→12) Disulfide A mixture of the peptidoresin of Example 1 (12 g.), anisole (20 ml.) and liquid hydrogen fluoride (200 ml.) was allowed to stand in an ice-bath (air excluded) for 50 minutes, after which excess hydrogen fluoride was removed under vacuo. The residue was extracted with 20% aq. acetic acid, and the extract was poured into 5 liters of deaerated water. The pH of the water was brought to 7.4 by adding dilute ammonium hydroxide, and the mixture was oxidized by adding a solution of $K_3Fe(CN)_6$ (1.5 g. in 500 ml. water). The oxidation mixture was acidified with glacial acetic acid to pH 5, and excess oxidant was removed by adding Bio Rad AG 3. The peptidic material was absorbed onto Amberlite CG-50 (H⁺ form) and then eluted with a mixture of water-acetic acid-pyridine (66:4:30 v/v). The fractions containing peptidic material were pooled and lyophilized to yield crude product, which was applied to a column of Sephadex G-25 (2.5×160 cm.) and eluted with 10% aq. acetic acid. Fractions 113 to 133 were collected and lyophilized to yield the title peptide, 855 mg.

TLC: Avicel coated glass plates, chlorox spray Rf n-butanol-water-glacial acetic acid, 4:1:1, v/v) 0.41.

Amino Acid Analysis: Thr (2) 1.87; Phe (3) 3; Cys (2) 1.49; Tyr (1) 0.87; Lys (1) 1.02; His (1) 0.89; Arg (1) 1.01; Trp (1) 0.67.

EXAMPLE 3 tert-Butyloxycarbonyl-S-p-Methoxybenzyl-L-Cysteinyl-N$^g$-Tosyl-L-Arginyl-γ-Benzyl-L-Glutamyl-L-Phenylalanyl-L-Phenylalanyl-D-Tryptophyl-N$^ε$-2-Chlorobenzyloxycarbonyl-L-Lysyl-O-Benzyl-L-Threonyl-L-Phenylalanyl-O-Benzyl-L-Threonyl-O-2,6-Dichlorobenzyl-D-Tyrosyl-S-p-Methoxybenzyl-L-Cysteinyl Hydroxymethyl Polystyrene Ester The above peptidoresin was prepared in a fashion similar to Example 1, substituting the requisite amino acid at the appropriate point in the synthesis.

EXAMPLE 4

L-Cysteinyl-L-Arginyl-L-α-Glutamyl-L-Phenylalanyl-L-Phenylalanyl-D-Tryptophyl-L-Lysyl-L-Threonyl-L-Phenylalanyl-L-Threonyl-D-Tyrosyl-L-Cysteine Cyclic (1→12) Disulfide Triacetate Salt The above dodecapeptide was prepared from the peptidoresin of Example 3 in a fashion similar to Example 2.

TLC: Avicel precoated glass plates.

$R_f$(n-Butanol-water-gl. acetic acid, 4:1:1, v/v) 0.57
$R_f$(n-Butano-ethyl acetate-water-gl. acetic acid, 1:1:1:1, v/v) 0.85
$R_f$(tert-Amylalcohol-pyridine-water, 7:7:6, v/v) 0.92.

Amino Acid Analysis: Thr (2) 1.96; Glu (1) 1.04; Cys (2) 1.79; Tyr (1) 1.02; Phe (3), 3; Lys (1) 1.04; Trp (1) 1.09; Arg (1) 1.01.

EXAMPLE 5 tert-Butyloxycarbonyl-S-p-Methoxybenzyl-L-Cysteinyl-N$^{im}$-Tosyl-L-Histidyl-N$^{im}$-Tosyl-L-Histidyl-L-Phenylalanyl-L-Phenylalanyl-D-Tryptophyl-N$^ε$-2-Chlorobenzyloxycarbonyl-L-Lysyl-O-Benzyl-L-Threonyl-L-Phenylalanyl-O-Benzyl-L-Threonyl-O-Benzyl-D-Seryl-S-p-Methoxybenzyl-L-Cysteinyl Hydroxymethyl Polystyrene Ester The above peptidoresin was prepared in a fashion similar to Example 1, substituting the requisite amino acid at the approprite point in the synthesis.

EXAMPLE 6

L-Cysteinyl-L-Histidyl-L-Histidyl-L-Phenylalanyl-L-Phenylalanyl-D-Tryptophyl-L-Lysyl-L-Threonyl-L-Phenylalanyl-L-Threonyl-D-Seryl-L-Cysteine Cyclic (1→12) Disulfide Triacetate Salt The peptidoresin of the previous Example 5, was treated in similar fashion as in Example 2 to provide the title compound.

TLC: Silica gel precoated glass plates.
$R_f$ (n-Butanol-ethyl acetate-water-gl. acetic acid, 1:1:1:1, v/v) 0.52.
Avicel precoated glass plates
$R_f$(n-Butanol-water-gl. acetic acid, 4:5:1, v/v) 0.60
$R_f$(tert-Amyl alcohol-pyridine-water, 7:7:6, v/v) 0.76.

Amino Acid Analysis: Thr (2) 1.98; Ser (1) 0.98; Cys (2) 1.64; Phe (3) 3; Lys (1) 1.1; His (2) 2.1; Trp (1) 0.84.

EXAMPLE 7

The ability of the compounds of this invention to inhibit the secretions of growth hormone, insulin, and glucagon can be demonstrated in the following test procedure:

Male albino rats are divided into two groups (e.g. nine rats per group). Each animal is administered sodium pentobarbital (Nembutal), I. P., at a dose of 50 mg/kg. Fifteen minutes later, one group received a S. C. injection of the test compound in saline (typically 5 to 200 μg/kg.), and the other group (control) receives saline alone. Ten minutes later, each animal is given a 0.5 ml. injection of arginine (300 mg/ml., pH 7.2) into the heart. Five minutes after receipt of the arginine, the animals are decapitated and blood is collected into Trasylol-EDTA. An appropriate aliquot of each sample is assayed for GH, glucagon, and insulin by radioimmunossay. GH is determined by the method of Sinha et al., Endocrinol., 91, 784 (1972); glucagon is determined by the method of Caloona and Unger, "Methods of Hormone Radioimmunoassay," Jaffe et al., Ed., Academic Press, New York, 1974, pages 317–330; and insulin is determined by the method of Hales and Randle, Biochem. J., 88, 137 (1963). The blood concentrations of growth hormone, glucagon, and insulin for the animals given the test compound are compared by standard statistical methods to the blood concentrations for the control group. Inhibition is demonstrated by a significant decrease in hormone concentration.

The results of the testing of the peptides of Examples 2, 4, and 6 are set forth below:

| Exp. | Compound | Dose (μg/kg) | GH (ng/kg) | Insulin μU/ml | Glucagon (pg/ml) |
|---|---|---|---|---|---|
| A | Control | — | 508 ± 13 | 298 ± 33 | 61 ± 8 |
|   | Example 2 | 100 | 181 ± 47+ | 154 ± 39+ | 22 ± 7* |
| B | Control | — | 234 ± 36 | 187 ± 21 | 41 ± 5 |
|   | Example 2 | 400 | 67 ± 13* | 70 ± 23* | 9 ± 1* |
| E | Control | — | 354 ± 57 | 336 ± 31 | 62 ± 10 |
|   | Example 4 | 200 | 81 ± 6* | 128 ± 33* | 41 ± 14 |
| F | Control | — | 363 ± 74 | 75 ± 8 | 162 ± 29 |
|   | Example 6 | 100 | 83 ± 16* | 60 ± 10 | 55 ± 12* |

+ = p < 0.05
* = p < 0.01

The ability of the compounds of this invention to provide prolonged inhibition of browth hormone can be demonstrated in the following test procedure:

Albino male rats are arranged in two groups (nine rats per group). One group received a subcutaneous (S. C.) injection of the test compound (typically 1 mg/kg.) in saline, and the other group received a S. C. injection of saline alone (control). Twenty minutes before the end of the test period (two to four hours after injection) each animal is given an I. P. injection of sodium pentobarbital, 50 mg/kg. At the end of the experiment, blood samples are taken from each animal by cardiac puncture, and each sample is mixed with Trasylol-EDTA. An aliquot of each sample is assayed for GH by radioimmunoassay. The blood growth hormone concentrations for the animals receiving the test compound are compared by standard statistical methods to the growth hormone concentrations for the control animals. Compounds considered long-acting product a significant decrease in blood growth hormone concentration at a dose of 1 mg/kg. at least two hours after injection.

When tested in the above-described test procedure, the compound of Example 2 gave the following test results:

| Exp. | Compound | Dose (μg/kg.) | Time (hour) | Plasma GH (ng/ml.) |
|---|---|---|---|---|
| C | Control | — | 2 | 213 ± 14 |
|   | Example 2 | 1000 | 2 | 89 ± 5** |
|   | Control | — | 4 | 182 ± 12 |
|   | Example 2 | 1000 | 4 | 101 ± 13** |
| D | Control | — | 5 | 337 ± 36 |
|   | Example 2 | 1000 | 5 | 230 ± 31+ |
|   | Control | — | 6 | 234 ± 24 |
|   | Example 2 | 1000 | 6 | 172 ± 34 |

** = p < 0.001
+ = p < 0.05

The results demonstrate that the compound of Example 2 shows prolonged inhibition of growth hormone.

What is claimed is:

1. A compound of the formula:

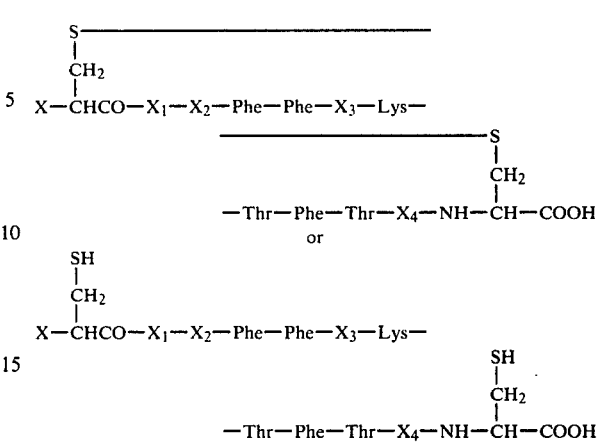

wherein:
X is H, —NH$_2$, —NH-Gly-Ala, —NH-D-Ala-Ala, —NH-Gly-Gly-Gly, —NH-acetyl, or —NH-benzoyl;
X$_1$ is His or Arg;
X$_2$ is His, Glu, Tyr;
X$_3$ is Trp, D-Trp, or 6-F-D-Trp; and
X$_4$ is D-Tyr or D-Ser;
or a non-toxic, pharmaceutically acceptable acid addition salt thereof.

2. A compound as defined in claim 1 which is L-cysteinyl-L-arginyl-L-histidyl-L-phenylalanyl-L-phenylalanyl-D-tryptophyl-L-lysyl-L-threonyl-L-phenylalanyl-L-threonyl-D-tyrosyl-L-cysteine cyclic (1→12) disulfide.

3. A compound as defined in claim 1 which is L-cysteinyl-L-arginyl-L-histidyl-L-phenylalanyl-L-phenylalanyl-D-tryptophenyl-L-lysyl-L-threonyl-L-phenylalanyl-L-threonyl-D-tyrosyl-L-cysteine.

4. A compound as defined in claim 1 which is L-cysteinyl-L-arginyl-L-α-glutamyl-L-phenylalanyl-L-phenylalanyl-D-tryptophyl-L-lysyl-L-threonyl-L-phenylalanyl-L-threonyl-D-tyrosyl-L-cysteine cyclic (1→12) disulfide.

5. A compound as defined in claim 1 which is L-cysteinyl-L-arginyl-L-α-glutamyl-L-phenylalanyl-L-phenylalanyl-D-tryptophyl-L-lysyl-L-threonyl-L-phenylalanyl-L-threonyl-D-tyrosyl-L-cysteine.

6. A compound as defined in claim 1 which is L-cysteinyl-L-histidyl-L-histidyl-L-phenylalanyl-L-phenylalanyl-D-tryptophyl-L-lysyl-L-threonyl-L-phenylalanyl-L-threonyl-D-seryl-L-cysteine cyclic (1→12) disulfide.

7. A compound as defined in claim 1 which is L-cysteinyl-L-histidyl-L-histidyl-L-phenylalanyl-L-phenylalanyl-D-tryptophyl-L-lysyl-L-threonyl-L-phenylalanyl-L-threonyl-D-seryl-L-cysteine.

8. A peptide-resin of the formula:

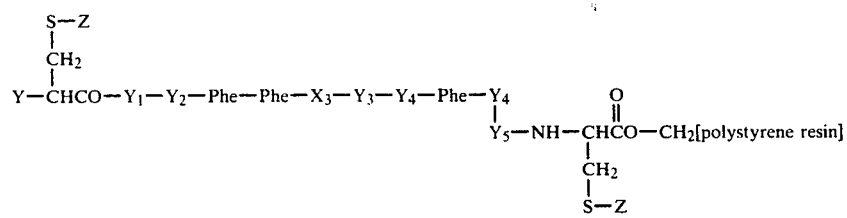

wherein:
(a) $X_3$ is Trp, D-Trp, or 6-F-D-Trp;
(b) Y is H, —NH(R), —NH-Gly-Ala(R), —NH-Gly-Gly-Gly(R), —NH-D-Ala-Ala(R), —NH-acetyl, or —NH-benzoyl;
(c) $Y_1$ is His($R_1$) or Arg($R_1$);
(d) $Y_2$ is His($R_1$), Glu($R_2$), Tyr($R_3$);
(e) $Y_3$ is Lys($R_4$);
(f) $Y_4$ is Thr($R_5$);
(g) $Y_5$ is D-Ser($R_5$), or D-Tyr($R_3$); and
(h) Z is the p-methoxybenzyl protecting group; wherein R is an α-amino protecting group and $R_1$, $R_2$, $R_3$, $R_4$, and $R_5$ are each, independently, a side-chain protecting group.

9. A peptide-resin as defined in claim 8 wherein:
R is t-butyloxycarbonyl;
$R_1$ is tosyl;
$R_2$ is benzyl(ester);
$R_3$ is 2,6-dichlorobenzyl;
$R_4$ is 2-chlorobenzoyloxycarbonyl; and
$R_5$ is benzyl(ether).

* * * * *